(12) United States Patent
Huiku

(10) Patent No.: US 7,215,994 B2
(45) Date of Patent: May 8, 2007

(54) MONITORING THE NEUROLOGICAL STATE OF A PATIENT

(75) Inventor: Matti Huiku, Espoo (FI)

(73) Assignee: Instrumentarium Corporation, Helsinki (FI)

( * ) Notice: Subject to any disclaimer, the term of this patent is extended or adjusted under 35 U.S.C. 154(b) by 384 days.

(21) Appl. No.: 10/780,360

(22) Filed: Feb. 17, 2004

(65) Prior Publication Data

US 2005/0182338 A1 Aug. 18, 2005

(51) Int. Cl.
*A61B 5/00* (2006.01)
(52) U.S. Cl. ...................... 600/544; 600/547
(58) Field of Classification Search ............... 600/544, 600/545
See application file for complete search history.

(56) References Cited

U.S. PATENT DOCUMENTS

| | | | | |
|---|---|---|---|---|
| 3,468,302 | A * | 9/1969 | Cowell | 600/547 |
| 4,570,640 | A * | 2/1986 | Barsa | 600/554 |
| 4,697,599 | A * | 10/1987 | Woodley et al. | 600/547 |
| 5,447,166 | A * | 9/1995 | Gevins | 600/544 |
| 6,016,444 | A * | 1/2000 | John | 600/544 |
| 6,042,548 | A * | 3/2000 | Giuffre | 600/483 |
| 6,120,443 | A | 9/2000 | Cohen-Laroque | |
| 6,571,124 | B1 * | 5/2003 | Storm | 600/547 |
| 6,622,035 | B1 | 9/2003 | Merilainen et al. | |
| 2002/0183605 | A1 | 12/2002 | Devlin et al. | |
| 2004/0243017 | A1 * | 12/2004 | Causevic | 600/544 |
| 2005/0059899 | A1 * | 3/2005 | Merilainen et al. | 600/544 |

FOREIGN PATENT DOCUMENTS

| | | |
|---|---|---|
| EP | 0 553 162 | 5/1997 |
| EP | 1273265 | 1/2003 |
| WO | WO 02/32305 | 4/2002 |
| WO | WO-2002/100267 | 12/2002 |
| WO | WO-03/086188 | 10/2003 |
| WO | WO-03/094726 | 11/2003 |

OTHER PUBLICATIONS

*Automatic Detection of Nausea Using Bio-Signals During Immerging in a Virtual Reality Environment*, Y. H. Nam et al., 2001 Proceedings of the 23rd Annual EMBS International Conference, Oct. 25-28, Istanbul, Turkey, pp. 2013-2015.
*Skin conductance correlates with perioperative stress*, H. Storm et al., Acta Anaesthesiol. Scand. 2002, 46: 887-895.
*Clinical implementation of advanced control in anesthesia*, D. A. Linkens et al., Transactions of the Institute of Measurement and Control 22,4 (2000), pp. 303-330.

* cited by examiner

*Primary Examiner*—Robert L. Nasser
*Assistant Examiner*—Karen E Toth
(74) *Attorney, Agent, or Firm*—Andrus, Sceales, Starke & Sawall, LLP

(57) ABSTRACT

The invention relates to monitoring the neurological state of a patient. In the method invention, both cortex- and subcortex-related biosignal data are obtained from the patient, the subcortex-related biosignal data including at least bioimpedance signal data. A first indicator is calculated based on the cortex-related biosignal data, the first indicator being indicative of cortical activity in the patient and a set of indicators is calculated based on the subcortex-related biosignal data indicative of subcortical activity in the patient, the set of indicators including at least a second indicator calculated based on the bioimpedance signal data. A composite indication is then produced based on the first indicator and on the set of indicators. The invention also concerns an apparatus and a sensor for monitoring the neurological state of the patient.

29 Claims, 8 Drawing Sheets

Clamper — 20
Cascade filter — 21
— 22
40

CURRENT FLOW FROM C TO M

M  R  C

A

V

MONITORING THE NEUROLOGICAL STATE OF A PATIENT

FIELD OF THE INVENTION

The present invention relates generally to a method and apparatus for monitoring the neurological state of a patient. As discussed below, neurological state here refers to a state which is described by indicators indicative of the quality or adequacy of anesthesia or sedation applied to the patient. One application of the method and apparatus is thus monitoring the condition of a patient under anesthesia or sedation. The invention also relates to a sensor for obtaining the biosignal data needed for the monitoring.

BACKGROUND OF THE INVENTION

In living organisms, biological processes generate different types of output signals, which are generally referred to as biosignals. Biosignals may be electrical, mechanical or chemical.

Bioelectricity is a broad field including measurements of biopotentials and bioimpedance. Biopotentials cover electricity created in life processes internal in tissues, while in bioimpedance measurements electric currents are supplied from an external source outside living tissues. Biopotentials thus generally refer to active processes, such as excitation of nerve and muscle tissues, whereas bioimpedance is related to passive properties of the tissue, such as the properties of the skin. However, these passive properties can also be related to electrical or other processes internal in tissues, even though the measurement does not directly utilize the electricity generated internally in tissues.

Neuromonitoring is a subfield of clinical patient monitoring focused on measuring various aspects of brain function and on changes therein caused by drugs commonly used to induce and maintain anesthesia in an operation room or sedation in patients under critical or intensive care.

Electroencephalography (EEG) is a well-established method for assessing brain activity by recording and analyzing the weak biopotential signals generated in the cortex of the brain with electrodes attached on the skin of the skull surface. The EEG has been in wide use for decades in basic research of the neural systems of the brain as well as in the clinical diagnosis of various neurophysiological diseases and disorders.

Electrocardiography (ECG) is another well-established method for assessing cardiac function by recording and analyzing the rather strong biopotential signals generated in the heart. The electrodes are attached on the skin of the chest with more peripheral references. The ECG is commonly used for diagnosing cardiac dysfunctions, various cardiac and circulatory diseases, and arrhythmia.

Electromyography (EMG) is a method for recording electrical biopotentials of muscles. In an EMG measurement, the electrodes are attached on the surface of the skin at a muscle group. An EMG signal is often recorded from the skull of the patient, whereby the recorded signal indicates both the activity of the facial muscle (fEMG) and the brain (EEG). As the frequencies of the EMG spectrum are usually high and above the frequencies of the brain activity, the signal components can be separated by methods of signal processing or spectral analysis from the EEG signal.

One of the special applications to which a significant amount of attention has been devoted during the past few years is the use of processed EEG signals for the objective quantification of the brain function for the purpose of determining the level of consciousness. The basic idea is to automatically detect if the subject or patient is asleep or awake. Specifically, this has become an issue, both scientifically and commercially, in the context of measuring the depth of anesthesia during surgery. The concept of the adequacy of anesthesia, which is a broader concept, further includes various other aspects relating to the quality of anesthesia, such as the state of the autonomic nervous system (ANS), and more specifically analgesia, i.e. loss of sensation of pain.

The need for reliably monitoring of the adequacy of anesthesia is based on the quality of patient care and on economy related aspects. Balanced anesthesia reduces surgical stress and there is firm evidence that adequate analgesia decreases postoperative morbidity. Awareness during surgery with insufficient analgesia may lead to a post-traumatic stress disorder. Prolonged surgical stress sensitizes the central pain pathways, which post-operatively increases patient pain and secretion of stress hormones. Low quality pre- and intra-operative analgesia makes it difficult to select the optimal pain management strategy later on. More specifically, it may cause exposure to unwanted side effects during the recovery from the surgery. Too light an anesthesia with insufficient hypnosis causes traumatic experiences both for the patient and for the anesthesia personnel. From economical point of view, too deep an anesthesia may cause increased perioperative costs through extra use of drugs and time, and also extended time required for post-operative care. Too deep a sedation may also cause complications and prolong the usage time of expensive facilities, such as the intensive care theater.

The assessment, measurement, or control of the different components of anaesthesia is 'a line drawn in water', as the drugs used in anaesthesia are often unspecific and influence many components simultaneously. The cortical components, i.e. hypnosis, amnesia and perception of pain and conscious control of movements, mainly refer to the activity of the cortex and integrity of the cortical evaluations of sensory afferent inputs and the ability to store information and control the body. Loss of consciousness, i.e. loosing responses to non-noxious sensory stimulations, such as spoken commands, is dominantly related to the overall suppression of cortical processing and awareness.

During the past few years, several commercial devices for measuring the level of consciousness and/or awareness in a clinical set-up during anesthesia have become available. These devices, which are based on a processed one-channel EEG signal, have been introduced by Aspect Medical (Bispectral Index), by Datex-Ohmeda (Entropy Index) and by Danmeter (an auditory evoked EEG potential monitoring device, AAI™). At present, the situation with the assessment of the cortical activity and integrity is considered satisfactory, though not resolved for all applications.

As to the central nervous system (CNS), the assessment or measurement of the suppression of the sub-cortical activity and integrity is far more unsatisfactory. No commercial devices exist for this purpose. This is mainly because the sub-cortical components are not represented in any single bioelectrical or other signal, in contrast to that the EEG almost alone may represent the cortical activity. The suppression of the sub-cortical components is demonstrated in at least two ways: first, in suppression of the sensory and pain pathways at sub-cortical level (i.e. suppressions of the afferent neuronal signaling) and, second, in suppression of the autonomic nervous system (ANS) control and reflexes (i.e. suppression of the efferent neurons and evaluations needed for efferent control at sub-cortical level).

The sub-cortical integrity of the afferent input, ANS evaluations, and efferent output is best tested with noxious stimulations and responses, as these are mainly processed and modulated in the brainstem and spinal levels. Further, as analgesic or antinociceptive drugs also have their main effects at these sub-cortical levels, the relationship between the analgesics, mainly opiods, and the suppression of the pain pathways and consequent noxious event responses exists.

International patent application WO 02/32305 discloses a method and device for ascertaining the cerebral state of a patient. In this disclosure, a measure derived from EMG signal data enhances and confirms the determination of the hypnotic state made using EEG signal data. As the EMG data may be computed more frequently than the EEG data, this renders ascertaining changes in the hypnotic state of the patient more rapid. In this method, the (facial) EMG thus alone reflects the suppression of the nociceptive pathways. State entropy (SE), which is calculated in the low frequency band up to 32 Hz, is dominated by the cortical EEG activity, while response entropy (RE), which also includes the high frequencies, represents both the cortical and muscle activity. The difference RE-SE is, therefore, a measure of the (f)EMG power, which will increase at nociception and is therefore a good measure of the suppression of the pain pathways. However, the above-mentioned dependency on the medication of the patient may render the method unusable in certain situations. As the (facial) electromyography signal is affected by neuro-muscular blocking agents (NMBAs), which suppress signaling at the nerve-muscle junctions, the EMG component of the measurement may vanish and render the method unusable, if the medication of the patient includes neuro-muscular blocking agents. It shall also be emphasized that the difference RE-SE is not specific to the suppression of the pain pathways but also reflects the overall activity following any arousals in the CNS. The fEMG signal is thus activated after non-noxious stimulation such as auditory stimulation and it is difficult to assess if any noxious components are present in the facial muscle response.

The present invention seeks to alleviate or eliminate the above drawbacks and to bring about a complementary method which may be used in situations where methods resting on EMG signal data are not usable.

SUMMARY OF THE INVENTION

The present invention seeks to provide a method and apparatus for monitoring the neurological state of a patient under anesthesia or sedation, which are usable in diversified situations regardless of the medication of the patients.

In the present invention, a composite indication of the neurological state of the patient is produced from a first indicator indicative of the activity related to the cerebral cortex of the patient and from a set of other indicators indicative of the activity related to the subcortex of the patient. The set includes one or more indicators, each being indicative of the subcortex-related activity in the patient The subcortex-related activity here refers to the activity in the area of the brainstem, the spinal cord and the peripheral nervous system of the patient. The corresponding biosignal data is obtained through the peripheral nervous system of the patient. In order to obtain a reliable result which is not affected by neuromuscular blocking agents, the set includes an indicator indicative of the changes in the bioimpedance of the patient. In the present invention, the assessment of the adequacy of analgesia is thus approached with a method, which rests on two different types of bioelectricity measurements: a biopotential measurement to obtain an indication of the cortex-related activity and a bioimpedance measurement to obtain an indication of the subcortex-related activity. In practice, the biopotential measurement is an EEG measurement, while the bioimpedance measurement is a skin conductivity (SC) measurement.

Thus one aspect of the invention is providing a method for monitoring the neurological state of a patient. The method includes obtaining cortex-related biosignal data and subcortex-related biosignal data from the patient, the subcortex-related biosignal data including at least bioimpedance signal data. The method further includes calculating a first indicator based on the cortex-related biosignal data, the first indicator being indicative of cortical activity in the patient, and calculating, based on the subcortex-related biosignal data, a set of indicators indicative of subcortical activity in the patient, the set of indicators including at least a second indicator calculated based on the bioimpedance signal data. The method also includes producing a composite indication based on the first indicator and on the set of indicators.

In further embodiments of the invention, the composite indication may be produced, in addition to the indicator calculated based on bioimpedance signal data, from an ECG indicator indicative of the heart rate of the patient or of changes therein, from an EMG indicator indicative of electromyographic activity in the patient, or from both the ECG indicator and the EMG indicator. In other words, the set of indicators indicating of the subcortex-related activity may include one, two, or three different indicators. Using several subcortex-related indicators the neurological state may be determined specifically and reliably for a variety of patients being administered drugs of different types.

Another aspect of the invention is that of providing an apparatus for monitoring the neurological state of a patient. The apparatus comprises means for obtaining cortex-related biosignal data and subcortex-related biosignal data from the patient, the subcortex-related biosignal data including at least bioimpedance signal data. The apparatus further includes means for analyzing the cortex-related biosignal data to obtain a first indicator indicative of cortex-related activity in the patient and means for analyzing the subcortex-related biosignal data to obtain a set of indicators indicative of subcortex-related activity in the patient, the set of indicators including at least a second indicator calculated based on the bioimpedance signal data. The apparatus further includes means for producing a composite indication based on the first indicator and the set of indicators.

A further embodiment the invention provides a sensor for obtaining biosignal data from a patient. The sensor includes a flexible substrate attachable onto the skin of a patient and an electrode array mounted on the flexible substrate, the electrode array comprising a first set of electrodes for obtaining cortex-related signal data from the patient and a second set of electrodes for obtaining subcortex-related biosignal data from the patient, the second set including a first plurality of electrodes for measuring a bioimpedance signal from the patient.

The biopotential and bioimpedance measurements may thus be integrated by making at least one electrode common to both measurements. In an integrated solution, the biopotential and bioimpedance measurements may be performed either simultaneously or on a time division basis.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 and 19 in the appended drawings, wherein.

DETAILED DESCRIPTION OF THE INVENTION

Figure 1:
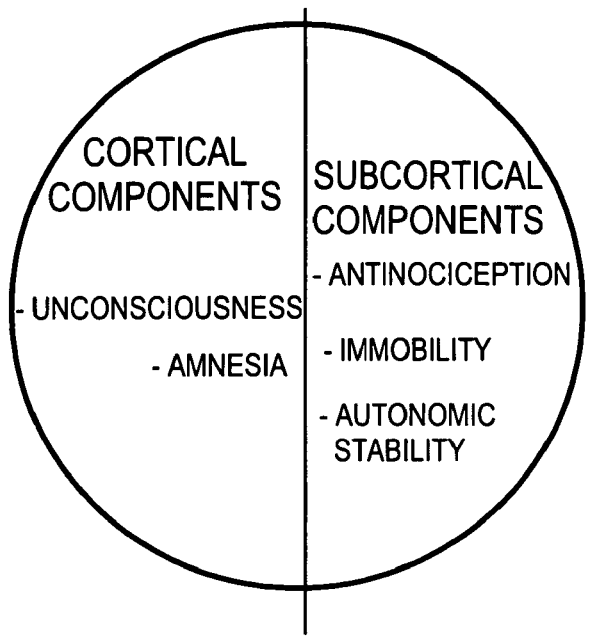
FIG. 1 illustrates the concept of quality of anesthesia.

FIG. 1 illustrates the concept of the quality of anesthesia. According to the current comprehension the quality of anesthesia includes five different components: hypnosis (i.e. unconsciousness), amnesia, antinociception, immobility and the stability of the ANS. The first two components, the hypnosis and amnesia, are of cortical origin and are indicative of cortical activities. The other components, which are indicative of sub-cortex related activity in the patient, are much more specific and often relate to altering of neural signaling at certain receptor or neurotransmitter level. For instance, the antinociception, i.e. the suppression of the neural transmission in the pain pathways, is achieved by opioid drugs, which affect the opioid/enkephalin receptors and activate the descending pathways, which block the nociceptive stimuli in the spinal cord. Furthermore, the NMBA drugs block the neural transmission in peripheral neuro-muscular junctions, which results in one kind of specific immobility of a patient. The stability of the ANS and the antinociception are closely related, since noxious stimulation in deep anesthesia causes hemodynamic and hormonal instability. The stability of the autonomic system is also advanced by several other drugs, which may affect specifically the parasympathetical or sympathetical activities of the ANS.

The present invention is based on the idea that a good measure of the depth of anesthesia is obtained by combining measurements that are indicative of both cortex- and sub-cortex-related activities. Therefore, skin conductance, which is indicative of the activity in the sympathetic nervous system, may be used for obtaining an indication of the subcortical activity and, combined with an indicator indicative of cortical activities, for obtaining a composite indication which is not affected by the neuro-muscular blocking agents.

As is discussed in U.S. Pat. No. 6,571,124, for example, the relationship between skin conductance and the activity in the sympathetic nervous system may be utilized for detecting pain. This is useful for patients that are unable to express the pain in a normal manner, such as premature babies that may lack the energy to cry and may have poorly developed facial expression.

In the present invention, bioimpedance and biopotential measurements are thus performed to produce a composite indication indicative of the neurological state of a patient. Before the actual method of the invention is discussed, typical arrangements for measuring biopotentials and bio-impedances are discussed briefly.

Figure 2:
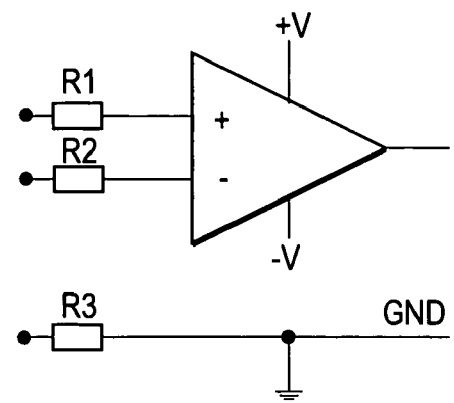
FIG. 2 illustrates a typical amplifier for measuring biopotentials.

FIG. 2 illustrates a typical amplifier for measuring biopotentials. The amplifier is supplied from a symmetrical power supply, e.g. +V and −V, with a ground potential in the middle. The amplifier is differential, i.e. signals are supplied to the non-inverted (plus) and the inverted (minus) input terminals, and an amplified differential signal is obtained from the output. Both input and output voltages are referred to ground (GND) potential (0 V). The input impedance of the differential amplifier is very high, typically greater than $10^9$ Ohms, and the input currents are minimal. The output has a low impedance (of the order of 10 Ohms), whereby high currents can be supplied to another electronic circuitry or to a load. The differential amplifier is an optimal choice for measuring weak biopotentials, such as ECG and EEG signals, with a three electrode sensor on the living tissue.

Figure 3:
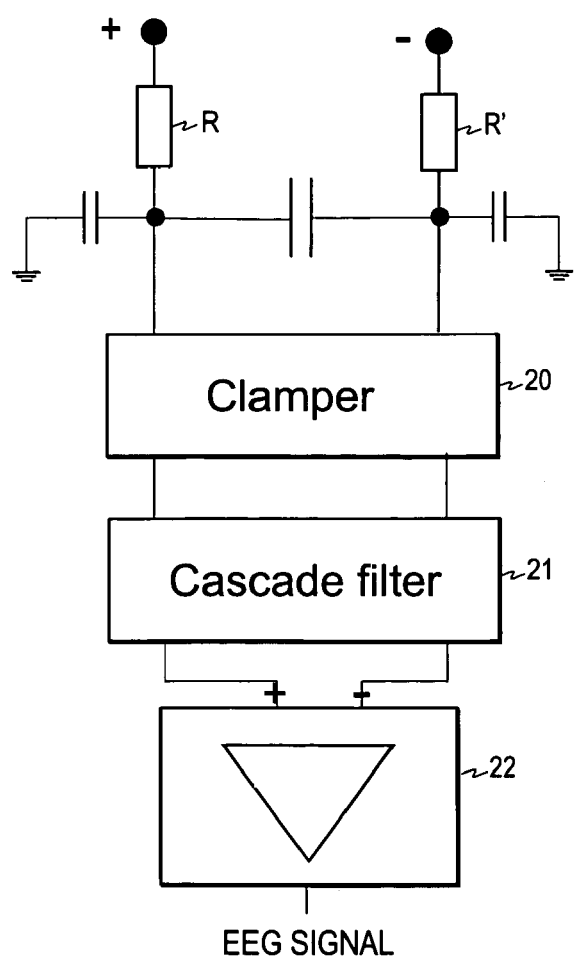
FIG. 3 illustrates one prior art measurement circuitry for EEG measurement.

FIG. 3 illustrates a typical one channel biopotential measurement circuitry utilizing a differential amplifier according to FIG. 2. The high impedance input electrodes on the skin of the patient are denoted by plus and minus signs, corresponding to the amplifier's inputs. The resistive components R and R' at the sensor input terminal describe the skin contact impedance with resistive electrode leads. On the electronic circuit board the input signals are usually first clamped in a damper 20, i.e. the input voltages are limited within the range of the circuit board supply voltages +V and −V. The input signal is then low-pass filtered for removing unwanted high frequency interference from the measurement signal and for improving the electromagnetic compatibility (EMC) characteristics of the measurement. This is usually performed by a cascade passive filter 21 including resistive and capacitive components. From the low-pass filter the signal is connected to an amplifier stage 22, which may thus include a different amplifier as shown in FIG. 2.

However, without a third reference voltage terminal this two terminal circuitry is sensitive to common mode voltages at the inputs, to drifting of the input voltages out of the supply voltage range, and to external noise interferences.

Figure 4:
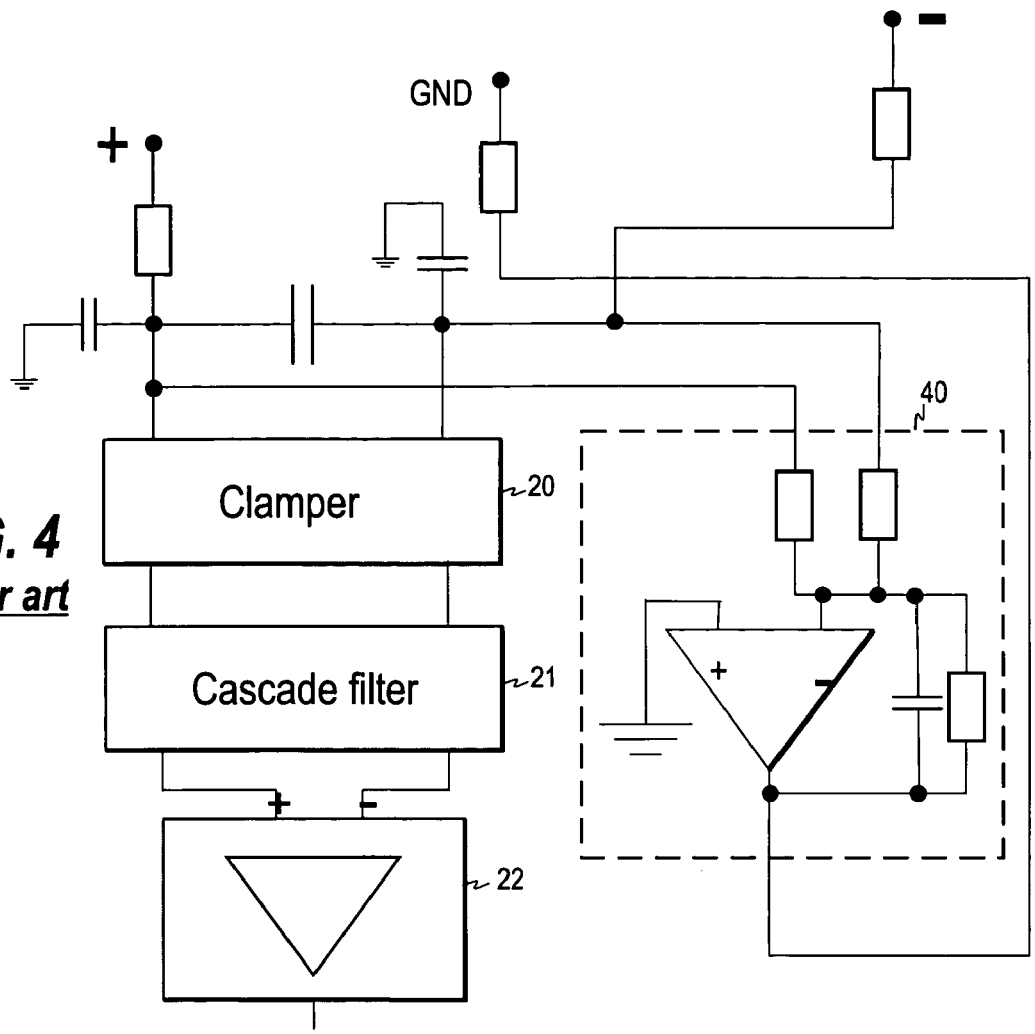
FIG. 4 illustrates another prior art measurement circuitry for EEG measurement.

FIG. 4 illustrates a circuit design, which greatly improves the performance of the two terminal biopotential measurement. A third terminal (GND) is added on the skin of the patient and the potential of this terminal is actively driven to an average voltage of the two high impedance inputs by means of an active reference circuit 40 including an amplifier. In this circuitry, the third terminal shall have a relatively high current drive capacity and, therefore, a low impedance for optimal performance. This circuit design eliminates a low frequency common mode voltage from the inputs, prevents the overflow of the voltages in the inputs, and also reduces external noise in the frequency range, in which the common mode voltages are compensated. Common mode voltages can be created by far field biopotentials, such as ECG signals, when the electrodes of an EEG measurement are on the skull of the patient. For optimal performance, the contact to the biopotential field shall be as good as possible, because any insulating material, such as the stratum corneum of the skin, between the conductive tissue (dermis and epidermis) and the electrode tend to uncouple the measurement from the biopotential field. The thicker the insulating material, the higher the input impedance of the amplifying device, because otherwise the amplifier tends to ground the electrode to circuit board ground potential instead of measuring the biopotential beyond the insulating layer. Therefore, the optimum performance of the biopotential measurement is obtained by electrodes, such as spikes penetrating the stratum corneum, which make a direct contact to the conducting tissue parts. An example of an electrode like this is described in U.S. Pat. No. 6,622,035 B1.

Figure 5:
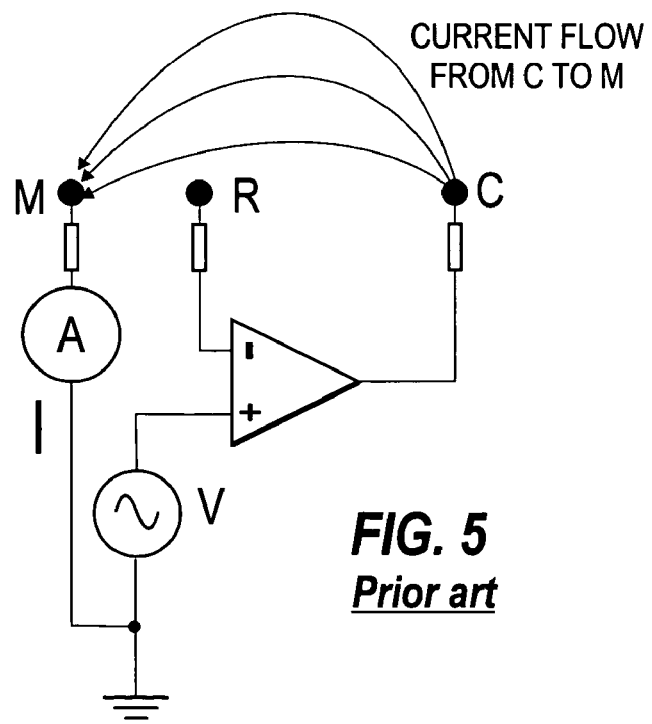
FIG. 5 is a schematic illustration of the principles of low impedance skin conductivity measurement.

FIG. 5 illustrates an example of a three electrode system for measuring skin impedance. In this measurement, only a zone of the current path proximal to the measuring electrode M is of interest. The sweat ducts under the measuring electrode will then effectively contribute to the skin impedance. In contrast to the biopotential measurement, a distal volume segment is a disturbance in this measurement. The electric current is supplied from the drive electrode C, which shall be of low impedance, as shall be the current receiving electrode M, too. With just these two electrodes the resultant current (with a constant voltage drive) is dependent on both the proximal local skin impedance at the two electrodes and on the tissue between. By adding a constant voltage drive electrode R near the measuring electrode M, only the skin under the measuring electrode will contribute to the impedance. The driving voltage at the drive electrode then sets to a value required to output current I=V/Z, where V is the constant voltage drive at electrode R (between R and M) and Z is the skin impedance under and near the measuring electrode M. The measurement result Z=V/I thus represents the skin impedance beneath the measuring electrode M.

The third electrode R is of high impedance (as the impedance is determined by the operational amplifier input). For optimal performance, the electrodes M and C shall be of low impedance, as they must carry a significant electric current. Furthermore, the high impedance electrode R must not load the electric field in the current path. Electrodes R and C must thus have as good a contact into the living conducting tissue as possible, but the current receiving electrode M shall not shunt the isolation layer of the stratum corneum. In other words, the shunt shall only be provided by the sweat secreted from the sweat glands under the skin and no other shunting mechanism must mask this primary measurement effect. Therefore, electrodes R and C can be spikes penetrating the stratum corneum, but measuring electrode M is optimally a large area plate (typically from 10 to 50 mm$^2$) on the clean non-conducting surface layer of the skin. Conducting gel is usually used between the measuring electrode M and the stratum corneum.

A skin conductivity (SC) measurement is thus technically different from the biopotential measurements (EEG, EMG), since in an SC measurement the electrodes of the sensor shall have a low source and sink impedance. In biopotential measurements, high electrode impedances are required for measuring the weak biopotential signals in order not to 'ground' the potentials under the electrodes, which would result in a very weak, unmeasurable, electric potential difference.

In the present invention, both biopotential and bioimpedance measurements are utilized for monitoring the neurological state of a patient. Although the patient is typically under anesthesia or sedation, the method may also be used when the patient, such as an infant, is not able to express his or her state in a normal manner. Furthermore, the method and apparatus of the invention may also be used to give an indication of the medication of the patient, as discussed below.

Figure 6:
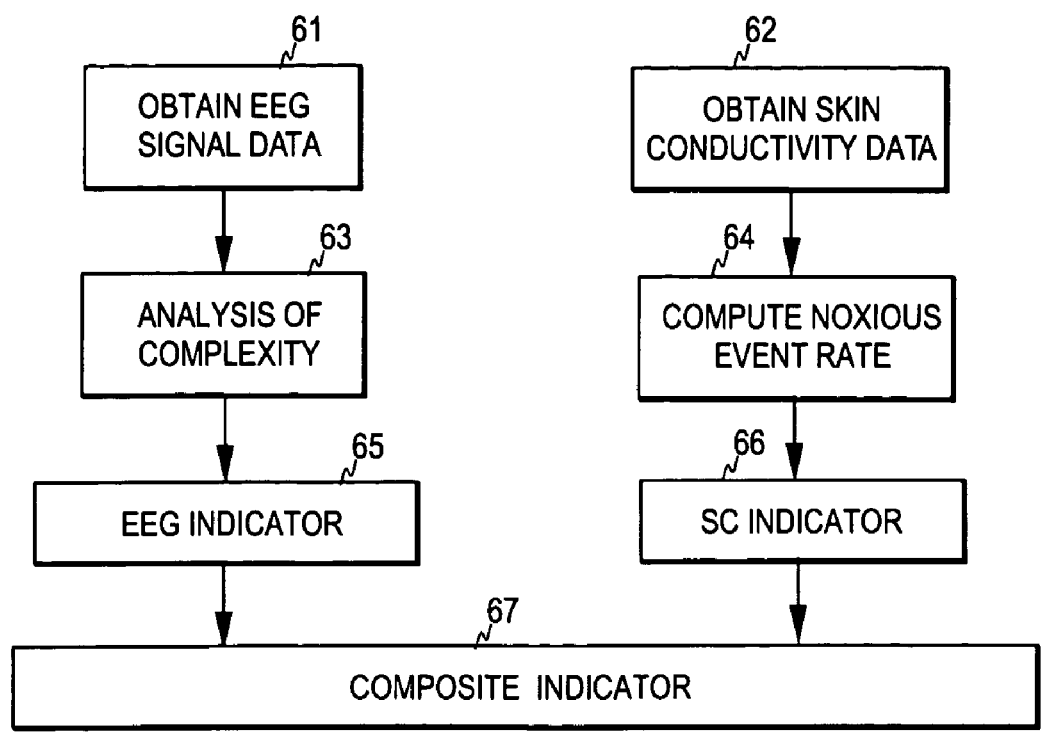
FIG. 6 is a flow diagram illustrating one embodiment of the invention.

FIG. 6 is a flow diagram illustrating one embodiment of the invention. First, EEG signal data and skin conductivity data are obtained from the patient (steps 61 and 62), the skin conductivity data being temporally related to the EEG signal data. The signal data may be collected in a conventional manner by converting the analog signals received from patient electrodes into digital format and storing the digital signals for further processing. The measurement circuitry preceding the AD conversion may be as shown in FIGS. 4 and 5. The processing of the digitized signals typically uses sets of sequential signal samples representing finite blocks of time, commonly termed "epochs". The frequency spectrum of the EEG signal is typically between 0.5 Hz and 30 Hz, while the skin conductivity signal is considerably slower, the spectrum being typically between 0.01 and 2 Hz. Although the EEG and SC signal data are stored prior to the being processed, the neurological state of the patient may be monitored almost in real-time. The speed of the measurement is mainly dictated by the slow SC signal.

The EEG signal data may then be processed, for example, as discussed in the above-mentioned patent application WO 02/32305. As noted there, relevant information with respect to the depth of anesthesia may be extracted from the EEG signal data by computing a parameter that characterizes the amount of disorder or complexity in the signal. Currently, the use of spectral entropy is deemed advantageous for this purpose due to the computational simplicity as compared to the other techniques available. However, other quantifications, such as fractal spectrum analysis, Lempel-Ziv complexity or bispectral or multispectral analyses may also be used for this purpose. As a more detailed discussion of the various mathematical techniques available for obtaining such a parameter can be found in the above-referred international patent application, these methods are not discussed in detail in this context. Thus at step 63 the complexity of the EEG signal is analyzed. This analysis yields an EEG indicator, such as the state entropy (SE) of the EEG signal, indicative of the activity of the brain of the patient (step 65).

The SC signal data, which is temporally related to the EEG signal data, is used to determine the rate of noxious events (step 64). The term noxious event here refers to such transients (local peaks) in the skin conductance of the patient, which exceed a certain threshold. The number of these peaks in a time window is indicative of the activity in the ANS, and more specifically in the sympathetic nervous system. The activity index obtained at step 66 thus represents the said number.

A composite indication of the state of the patient is then produced from the SC indicator and the EEG indicator at step 67. Although this may involve calculation of a single, combined parameter or index based on the two indicators, it is also possible that the production of the composite indication involves presenting the two indicators simultaneously to the user of the apparatus so that the user may assess their relative magnitudes. For example, two columns may be displayed to the user, the height of the first column indicating the value of the EEG indicator and the height of the second column indicating the value of the SC activity indicator. The nursing staff may then evaluate the neurological state of the patient based on the total and relative heights of the two columns.

Figure 7:
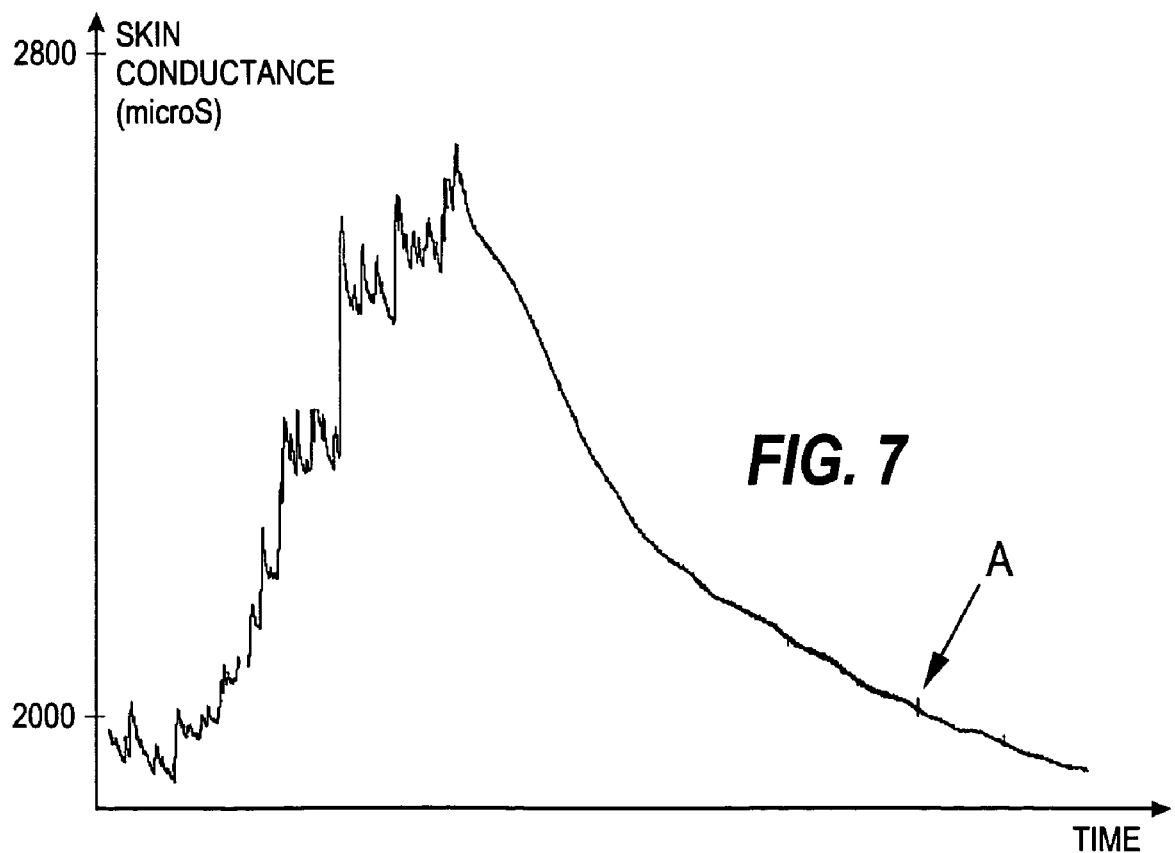
FIG. 7 illustrates an SC signal obtained from a patient.

As to the SC signal data, the changes in the skin conductivity are monitored and the rate of these changes is calculated. FIG. 7 illustrates a typical SC signal obtained from a patient when the patient is first in a conscious state and then moves to an unconscious state.

As can be seen from the figure, the changes in the skin conductivity appear as upward bursts. Each burst includes a steep rise resulting from the filling of the sweat ducts, followed by an exponential decay resulting from the evaporation and reabsorption of the sweat back into the skin. The frequency of the bursts is proportional to the activity in the autonomous nervous system of the patient. As is obvious from the figure, the activity is high in a conscious state and it is considerably suppressed at the transition to unconsciousness. In the unconscious state the bursts appear only at noxious stimuli. As indicated by arrow A in the figure, the amplitude of the bursts is also strongly suppressed in the unconscious state.

Figure 8:
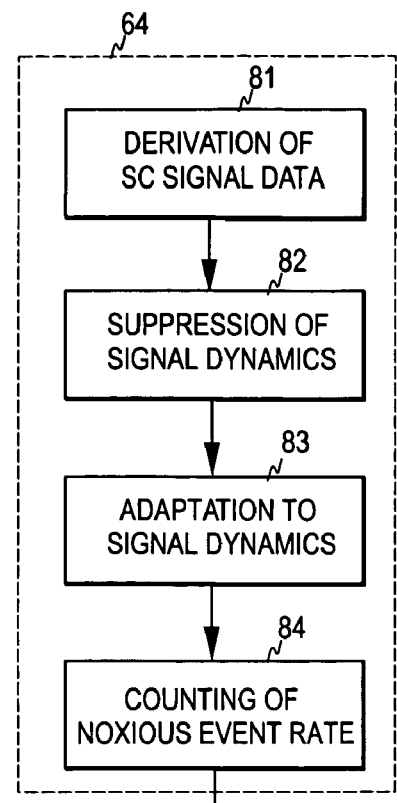
FIG. 8 is a flow diagram illustrating the calculation of an SC indicator in one embodiment of the invention.
Figure 9:
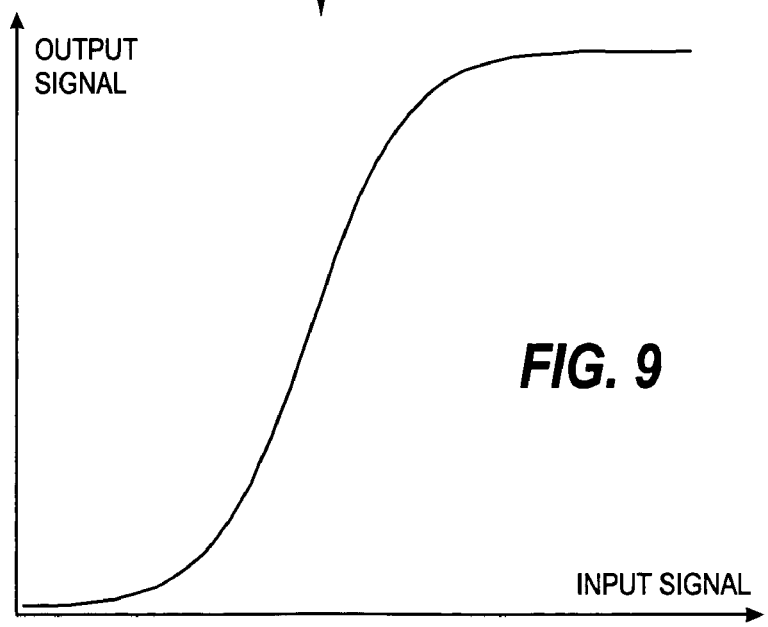
FIG. 9 illustrates the suppression of the signal dynamics in the SC measurement.

FIG. 8 illustrates the calculation of the rate of the peaks in the SC signal, i.e. noxious events, at step 64. First, the SC signal data is derived (differentiated) in order to extract the peaks from the SC signal data (step 81). Each peak in the derivative signal data then indicates a sympathetical activation, i.e. activity in the sympathetical nervous system. Since in the unconscious state the magnitude of an activation is very small, the small values of the derivative signal data are first enhanced in order to facilitate the counting of the events. The dynamics of the derivative signal data is therefore suppressed at step 82. This may be implemented, for example, by amplifying the signal data by a sigmoid function producing input-output characteristics according to FIG. 9. As can be seen from the input-output characteristics, high input signal values are attenuated in comparison to low input signal values.

Figure 10:
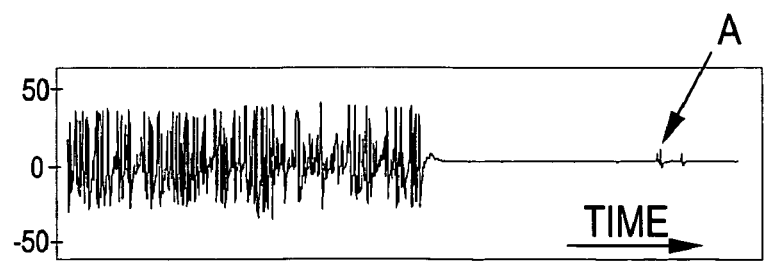
FIG. 10 illustrates the signal of FIG. 7 after the suppression of the signal dynamics.

It is advantageous to set the parameters of the amplifying sigmoid function in such a way that the noise level of the device is about one half of the signal value producing zero output, which corresponds to the center of the sigmoid curve. The low signal values higher than the noise level are then enhanced, while the values much larger than that are suppressed. As a result of the suppression of the dynamics, the changes in the SC signal are equalized. FIG. 10 illustrates the signal of FIG. 7 after the derivation and the suppression of the signal dynamics.

Figure 11:
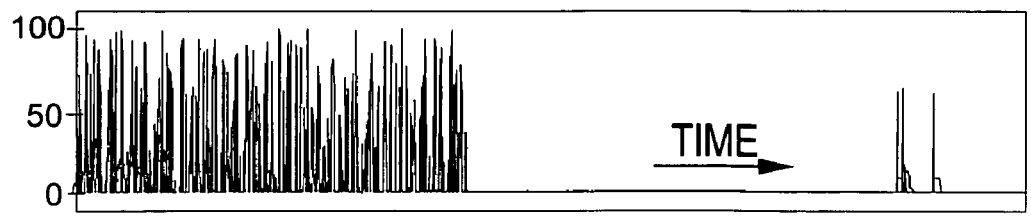
FIG. 11 illustrates the signal of FIG. 7 after a histogram transformation according to one embodiment of the invention.

In addition to the above suppression of the signal dynamics, it is advantageous to perform an further adaptation to signal dynamics (step 83) in order to "force" the values of the output signal to a certain value range regardless of the values of the input signal. This may be implemented by performing a histogram transformation for the signal data, i.e. the histogram of the raw signal data values is transformed into a new distribution of the data values, which can correspond to, for instance, a gaussian signal in certain time interval. In the histogram transformation, signal data measured over a time window is sorted in an ascending order, whereby an array is formed in which the lowest signal value corresponds to a lowest index, for example one, and the highest signal value corresponds to a highest index, such as one hundred assuming that the array includes one hundred signal values. The value of each new data point obtained from the SC signal data is then transformed to correspond to its index in the sorted array. In this way, the level of the SC signal may change but the output values remain between the said lowest and highest indices. The median value, i.e. the center index, is usually transformed to zero output. The distribution of the output values can be specified according to the needs of the application. In the noxious event counting it is advantageous that the output distribution is Gaussian, in which case the counting threshold can be selected to correspond to the standard deviation of the output values. This means that the event counter is incremented, when the input value belongs to the upper 16 percent of the sorted input array (68 percent of data points in between the positive and negative standard deviation). Other threshold values may be selected in order to increase or decrease the counting rate. FIG. 11 presents the histogram transformed data of FIG. 10. Negative values are cut to zero and each positive value indicates a possible noxious event. When the threshold value is set at one standard deviation a noxious count is registered, if the transformed signal exceeds about a value of 50.

Figure 12:
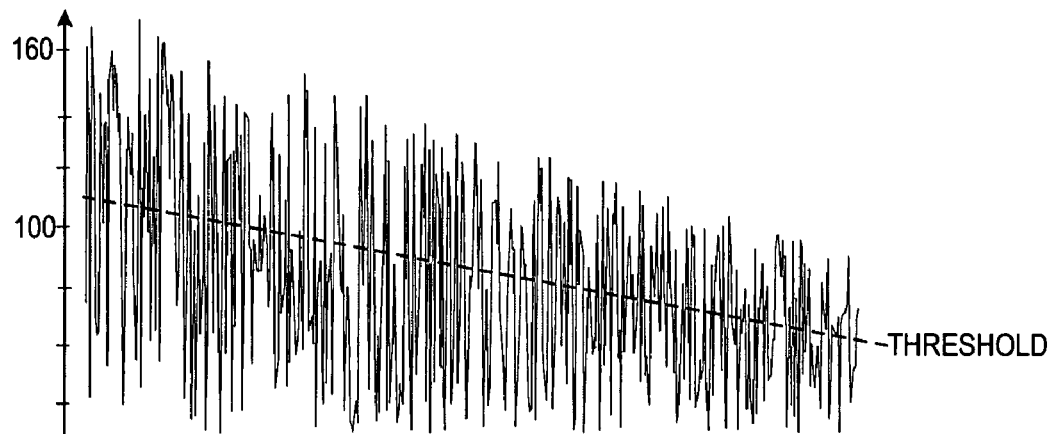
FIG. 12 illustrates the effect of the histogram transformation on the SC signal.

FIG. 12 demonstrates the effect of the histogram transformation in one embodiment of the invention. The input data values (on top in the figure) are evenly distributed (random numbers) over a short time window, but the span of the values is continuously decreasing with time. The output values (on bottom) are Gaussian with constant standard deviation. The length of the input buffer determines the time, over which the signal is Gaussian and the mean value zero. This constitutes the memory of the histogram transformation, i.e. the transformation does not store signal values that are farther in the past than the length of the input memory. Two criteria must be obeyed in constructing the memory for the transformation. First, the above-mentioned time window must be sufficiently long in order to include enough data in the input buffer. Usually a window between 100 and 200 seconds is practical. Second, the input buffer shall be updated only when the input value is outside of the noise signal limits. This means that the transformation is learning, i.e. adapting to the signal, only when there are new bursts in the input data. However, it is continuously adapting to the input values as long as they are large enough to be distinguished from the noise background.

After the histogram transformation is performed for the signal data, the rate of the noxious events is computed at step 84 where the transformed values are compared to a fixed threshold value and the number of values exceeding the threshold in a time unit is determined. Even though a fixed threshold value (T1 in FIG. 12) is thus used for the transformed SC signal, the histogram transformation causes the threshold to continuously adapt to the input signal values, as shown by a dashed line in FIG. 12. In this way, the determination of the SC indicator is independent of the level of the SC signal.

Figure 13:
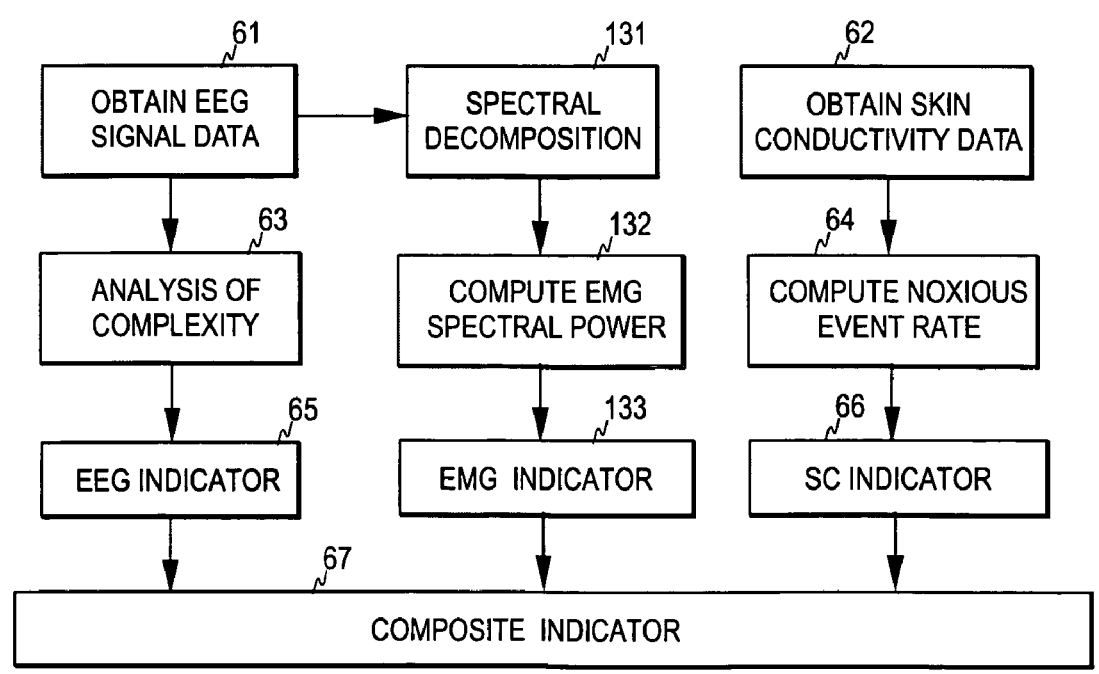
FIG. 13 is a flow diagram illustrating a further embodiment of the invention.

In another embodiment of the invention, EMG data may also be used to determine an EMG indicator indicative of the electromyographic activity in the patient. When the level of anesthesia approaches inadequacy, a painful stimulus causes the frontalis muscle to contract, which can be detected from the EMG signal. FIG. 13 illustrates this embodiment, in which an EMG indicator is determined, in addition to the above-discussed EEG and SC indicators. The EMG indicator may be determined, for example, by calculating the power spectrum of the EMG signal data, as described in the above-mentioned patent application WO 02/32305. The power spectrum provides an indication of the EMG activity, i.e. an EMG indicator at step 133. The EMG signal data may be obtained from the EEG signal data by subjecting the EEG signal data to spectral decomposition (step 131) or by using a separate measurement signal (i.e. measuring electrodes) for the EMG signal data. The three indicators are then used to produce a composite indication of the state of the patient. The use of the EMG or the SC branches may also be selectable so that the nursing staff may select whether the apparatus uses all three indicators, or two indicators only (EEG+SC or EEG+EMG). Depending on the medication of the patient, the nursing staff may then decide whether the EEG and the SC or the EEG and the EMG indicators are used. This kind of apparatus is versatile in being suitable for patients with different types of medication.

Figure 14:
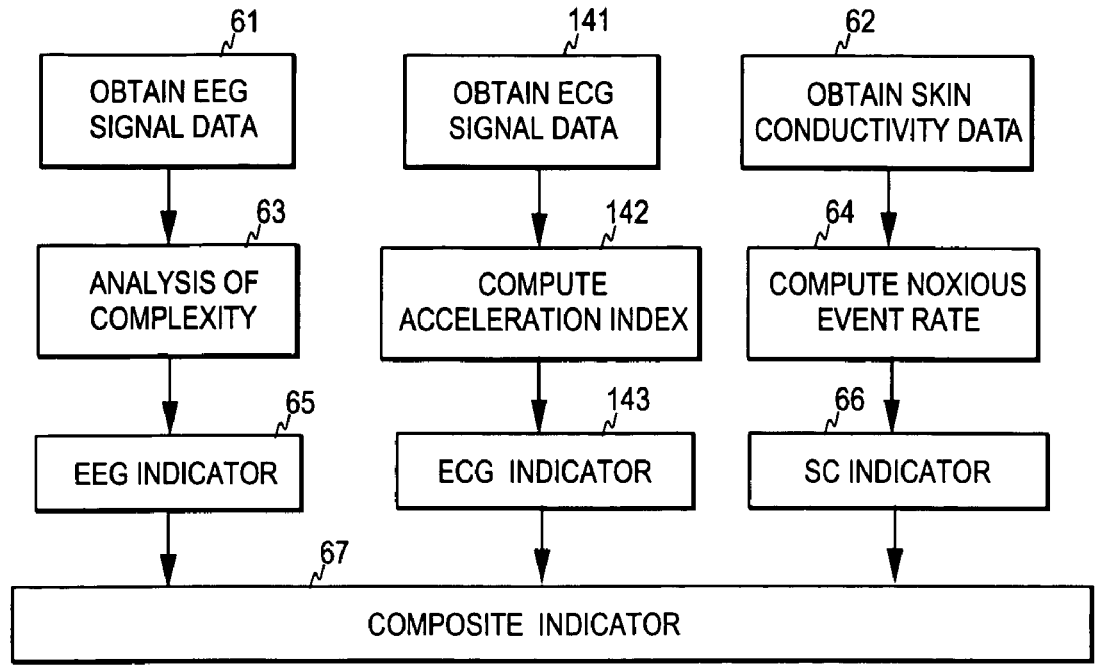
FIG. 14 is a flow diagram illustrating a still further embodiment of the invention.

In a further embodiment of the invention, the EMG measurement is replaced by a heart rate (HR) measurement as shown in FIG. 14. The EMG signal data is thus replaced by ECG signal data. Based on the ECG signal data, an ECG indicator may be calculated at step 142. The ECG indicator is indicative of one or more attributes related to the heart rate of the patient. Various indicators may be calculated for this purpose, such as parameters describing the absolute heart rate (HR) or the heart rate variability (HRV), the respiratory sinus arrhythmia (RSA) of the patient, for example. A further parameter usable as an ECG indicator is a heart rate acceleration index. The calculation of the heart rate acceleration index may be performed as disclosed in EP Patent Application EP 1 273 265, for example. The heart rate acceleration index and the other above-mentioned heart rate related indicators are indicative of sympathetic activation caused by pain, and they may therefore be used instead of the EMG indicator in the apparatus.

It is also possible to utilize both the EMG signal data and the HR signal data together with the SC signal data for obtaining an indication of the subcortical components of the neurological state of the patient.

The method of the invention may also be utilized for controlling the administration of medication to the patient. When the drug strategy has been selected for a surgery by an anaesthesiologist, and when the cortical, i.e. hypnotic, and the subcortical, i.e. analgesic, indicators of the neurological state of the patient are available for instance through the above measurements of the EEG spectral entropy and the skin conductivity, the actual drug administration can be automatically guided in a closed loop control system, where the said indicators of the invention continuously provide feedback information for the administration process. The above-described indicators indicative of cortical and subcortical activities may thus provide the simultaneous measurements of the hypnotic and analgesic effects needed in a closed loop control of the infusion of specific hypnotic and analgesic drugs for achieving balanced anaesthesia at all times.

In a further embodiment the invention thus provides an indicator for the hypnotic state by measuring EEG biopotentials and a set of indicators indicative of the subcortical analgesic state by measuring skin conductivity and/or other indicators, such as the heart rate indicator and/or the EMG indicator, for balancing the delivery of hypnotic and analgesic drugs. For instance, the anaesthesiologist may decide to increase the delivery of an analgesic drug in situations, in which the EEG entropy is adequately low, but the patient still responses to surgical stress by increased subcortical activity. On the other hand, in situations with higher entropy in the upper range of the targeted entropy values, the delivery of a hypnotic drug may be increased, possibly accompanied with an increased delivery of opioids if the increased delivery of the hypnotic drug is not enough for reaching a desired state. In addition to using the invention as a decision-making support tool for an anesthesiologist, the indicators of the cortical and subcortical state of a patient may thus directly control the device(s) delivering hypnotic and analgesic drugs in a closed control loop.

Figure 15:
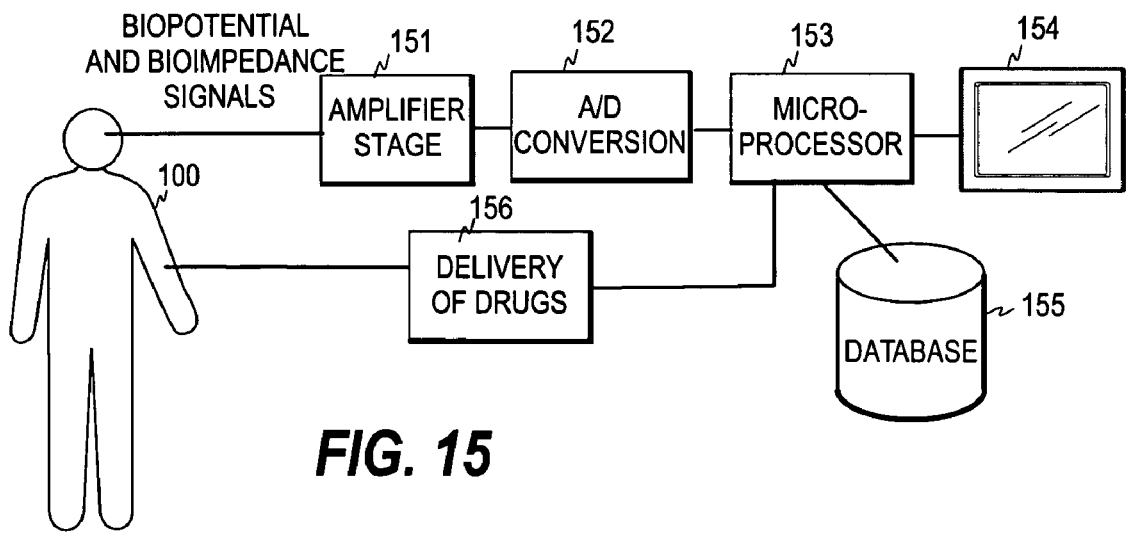
FIG. 15 illustrates one embodiment of the system according to the invention.

FIG. 15 illustrates one embodiment of the system according to the invention. The biopotential and bioimpedance signals obtained from one or more sensors attached to a patient 100 are supplied to an amplifier stage 151, such as amplifier stage 22 in FIG. 4, which amplifies the signals before they are sampled and converted into digitized format in an A/D converter 152. The digitized signals are supplied to a microprocessor 153 which may then carry out the detection and rejection of artifacts.

The microprocessor is provided with a database or memory unit 155 holding the digitized signal data obtained from the sensor(s). The microprocessor computes the above-described indicators, produces a composite indication, and displays the results on the screen of a monitor 154 connected to the microprocessor. As discussed above, the composite indication may be displayed in various ways using graphical and/or numeric or textual information. As also discussed above, the microprocessor may further supply indicators indicative of the cortical and subcortical activity in the patient as input data to a device or system 156 delivering drugs to the patient.

The above embodiments thus require different types of measurements. This, in turn, normally requires different types of electrodes as discussed in connection with FIGS. 4 and 5. In one embodiment, the invention provides a mechanism for decreasing the number of electrodes, which will improve the usability of the sensor of the measuring apparatus. This is discussed in the following.

Figure 16:
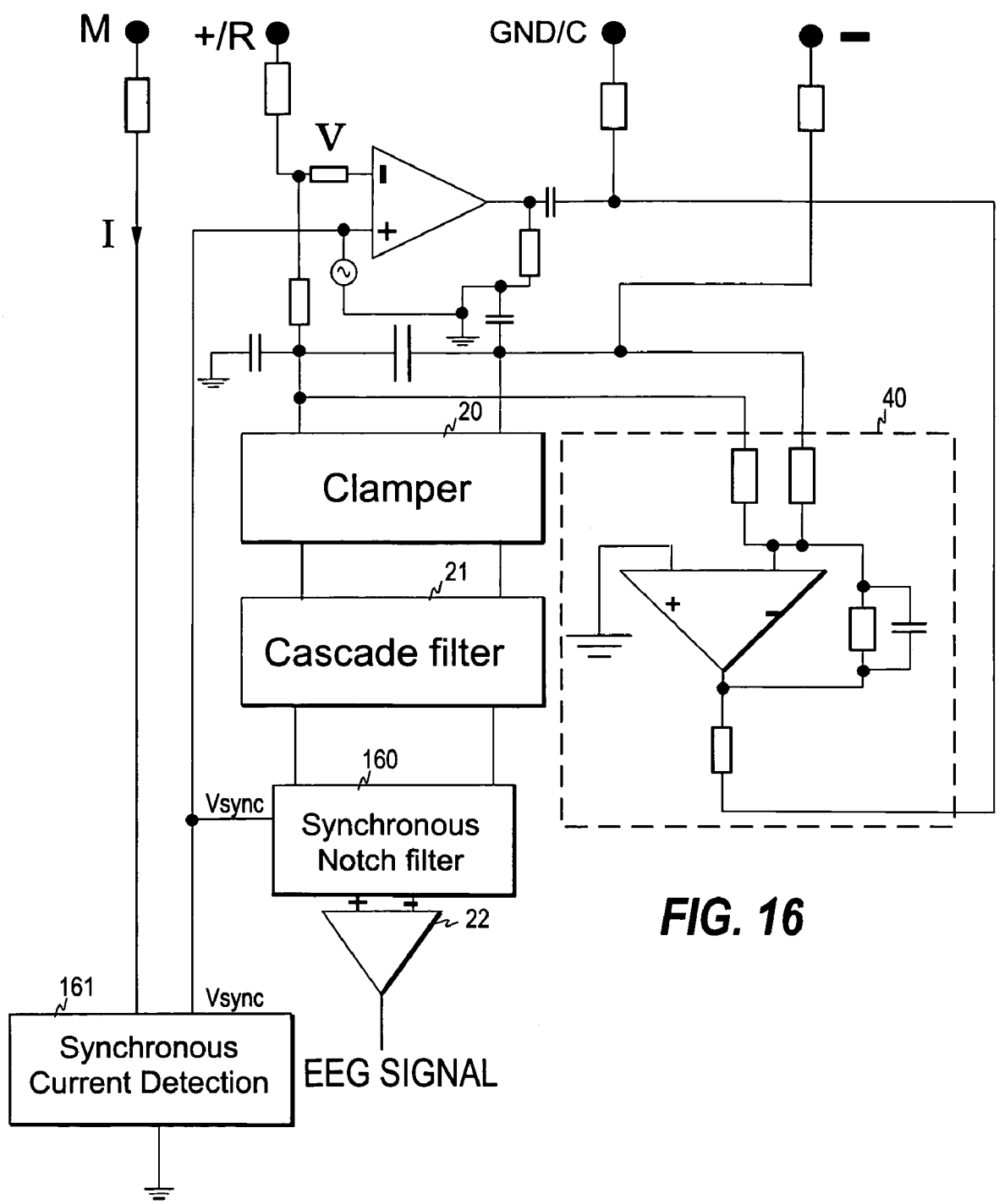
FIG. 16 illustrates a combined EEG and SC measurement according to one embodiment of the invention.

FIG. 16 illustrates one embodiment for obtaining the biopotential (EEG+EMG or ECG) and the bioimpedance (SC) data. Normally, this kind of a combination requires six electrodes, three for the biopotential measurement as shown above in FIG. 4, and three for the bioimpedance measurement as shown above in FIG. 5. In the embodiment of FIG. 16, the third electrode R of the bioimpedance circuitry and the "plus" electrode of the biopotential measurement, i.e. two high impedance electrodes, are combined. Similarly, the ground electrode (GND) of the biopotential circuitry and the current drive electrode (C) of the bioimpedance circuitry, i.e. two low impedance electrodes, are combined to one electrode. It is essential that the voltage drive of the impedance measurement does not disturb the biopotential measurement. In the embodiment of FIG. 16, this can be ensured in the following way: the bioimpedance measurement uses an alternating narrow-band (in practice sinusoidal) drive voltage (with zero mean), which is filtered out from the broadband biopotential measurement signal. The drive frequency may be selected to be above the biopotential frequencies (e.g. >100 Hz), in which case a low-pass filter circuitry can be used.

In the embodiment of FIG. 16, however, the drive frequency (e.g. 75 Hz) may be in the biopotential frequency range or near that range (EEG typically from 0 to 30 Hz and EMG from 10 to 150 Hz), since a very narrowband notch filter 160 receiving a synchronizing reference voltage Vsync is used to filter out the bioimpedance component of the measurement from the combined EEG+EMG signal. For this purpose, so-called switched capacitor single chip filters can be used, for example. The bioimpedance may be detected, for example, by lock-in techniques, in which the drive voltage V serves as a reference signal from which a current detection circuit 161 generates the synchronization signal (Vsync) for the notch filter. In other words, synchronous detection is used to separate the bioimpedance component from the biopotential signal. The common mode rejection circuitry of the embodiment of FIG. 16 shall be tuned to reject common mode signals well below the frequency of the impedance measurement. This does not compromise the performance as the common mode signals are usually of very low frequency, in practice DC.

In the embodiment of FIG. 16, the biopotential signal and the bioimpedance signals may be measured simultaneously. However, the circuitry may be simplified considerably, if the skin conductivity measurement is done intermittently with the biopotential measurement. One simple realization of such a measurement circuitry, shown without the common mode cancellation, is presented in FIG. 17. The time between the two measurements can be divided according to the needs of the frequency band of the SC and EEG signals. The changes in the SC signal are normally very slow and, in practice, an SC value is needed only once in a half of a second. According to the Nyqvist theorem, the signal bandwidth up to 1 Hz can then be measured, which is enough for most SC applications. The time division can then be such that the EEG signal is recorded in epochs of about 0.5 sec and each of these blocks are separated by one single SC measurement taking a few hundred milliseconds depending on the measurement frequency (which in this case could be about 100 Hz, for example). The switching between the measurement modes can be done, as exemplified in FIG. 17, by closing switch 171 for recording the SC signal. When a switch is closed, a constant a.c. current is supplied to one of the "plus" and "minus" electrodes ("minus" electrode in FIG. 17), and the voltage is measured, using the EEG detection amplifier, from the other electrode ("plus" in FIG.17). The circuitry thus has two modes: a first mode in which two of the electrodes are high impedance electrodes (biopotential measurement, switch open) and a second mode in which two of the electrodes are low impedance electrodes (bioimpedance measurement, switch closed).

Figure 17:
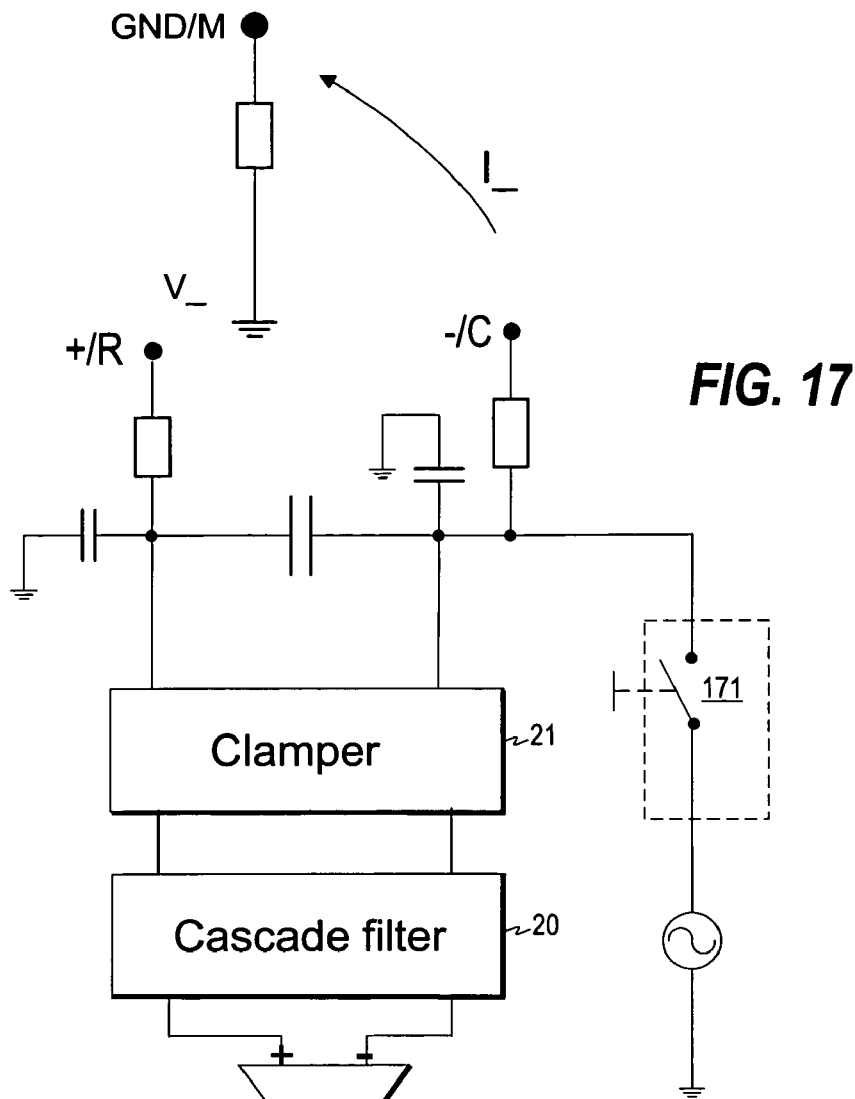
FIG. 17 illustrates a combined EEG and SC measurement according to another embodiment of the invention.

In the embodiment of FIG. 17, the bioimpedance is thus measured by supplying a constant current to the drive electrode and measuring the corresponding voltage, while in the embodiment of FIG. 5 a constant voltage is supplied and the correspondent current is measured. However, if a constant voltage drive is preferred, the current measuring circuit, such as shown in FIG. 16, can be set to read the GND terminal directly. As the EEG signal is relatively far field (a large electric dipole) and the SC measurement shall be as local as possible, the electrode configuration of FIG. 17 cannot be optimized for both, usually a large electrode distance is preferred for better signal-to-noise in EEG. However, even though the tissue impedance between the electrodes will contribute to the SC value, the skin impedance changes due to sweating can still be detected. It shall also be noted that the GND electrode can be located quite near the driving electrode ("minus" in FIG. 17), which minimizes the tissue impedance.

Figure 18:
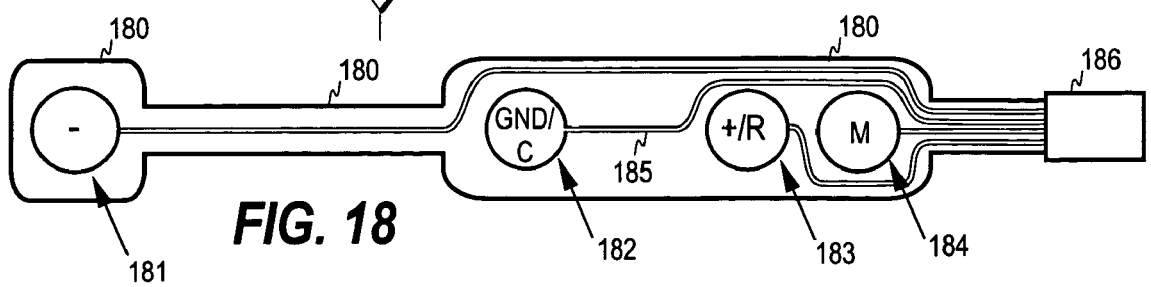
FIG. 18 illustrates one embodiment of a sensor according to the invention.

FIG. 18 is a top view of one embodiment of a sensor according to the invention. In this case, the sensor is suitable for the measuring arrangement of FIG. 16. The sensor comprises a thin and flexible substrate 180 made of plastic material, for example. The thickness of the substrate is typically below 0.5 mm. Four electrodes 181 to 184 are integrated onto the surface of the substrate, each electrode being provided with a respective connector 185 connecting the electrode to a terminal 186 at one end of the sensor. The terminal can be connected with a mating terminal at the end of a measurement cable (not shown) connected to the amplifier state of the measuring apparatus. The connectors may be printed on the substrate. The electrodes form an array in which they are located in the order shown in FIG. 16. The first electrode 181, which is the farthest from the terminal, is the electrode operably connected to the inverted branch of the EEG amplifier stage for measuring the EEG signal data, the second and third electrodes 182 and 183 are the above-described combined electrodes, and the fourth electrode is the measuring electrode M of the skin conductivity measurement. The first electrode is clearly apart from the other electrodes and, as discussed in connection with FIG. 5, the third and fourth electrodes are close to each other in order to ensure that only the skin under the measuring electrode will contribute to the skin conductivity measurement. The sensor can be attached to the patient so that the second, third and fourth electrodes are on the forehead of the patient, while the first electrode is in the temple area of the patient. The widened portions of the substrate around the sensors may be provided with an adhesive coating for adhering the sensor to the skin of the patient.

Figure 19:
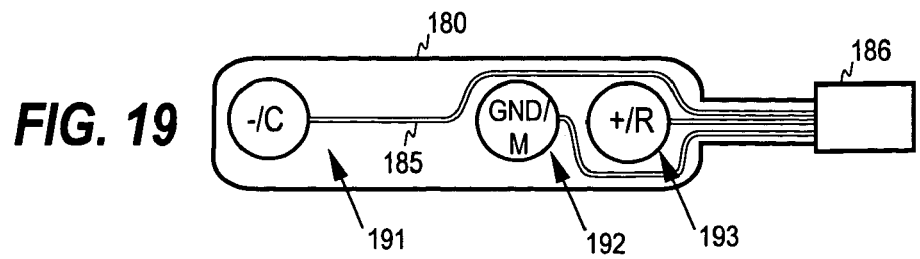
FIG. 19 illustrates another embodiment of a sensor according to the invention.

FIG. 19 is a top view of another embodiment of a sensor according to the invention. In this case, the sensor is suitable for the measuring arrangement of FIG. 17. The electrode array now includes three electrodes 191 to 193, which are all combined electrodes as shown in FIG. 17. The sensor of FIG. 19 thus requires a measurement arrangement according to FIG. 17.

Although the invention was described above with reference to the examples shown in the appended drawings, it is obvious that the invention is not limited to these, but may be modified by those skilled in the art without departing from the scope and spirit of the invention. For example, the suppression of the signal dynamics or the adaptation to the signal dynamics may be omitted when calculating the SC indicator.

The invention claimed is:

1. A method for monitoring a state of anesthesia or sedation resulting from the administration of one or more drugs to a patient, the drug or drugs inducing the state of anesthesia or sedation by altering the state or functioning of one or both of the cortex of the brain or the sub-cortical components of the nervous system, the method comprising the steps of:
   (a) obtaining cortex-related EEG biopotential signal data from the patient;
   (b) obtaining subcortex-related biosignal data from the patient, the subcortex-related biosignal data including at least bioimpedance signal data;
   (c) calculating a first indicator comprising a measure of the complexity of the EEG biopotential signal data, the first indicator being indicative of cortical activity in the patient;
   (d) based on the subcortex-related biosignal data, calculating a set of indicators indicative of subcortical activity in the patient, the set of indicators including at least a second indicator calculated based on the bioimpedance signal data; and
   (e) producing a composite indication based on the first indicator and on the set of indicators.

2. A method according to claim 1, wherein:
   step (d) includes calculating only the second indicator; and step (e) includes producing the composite indication from the first indicator and the second indicator.

3. A method according to claim 1, wherein
step (b) further includes obtaining ECG signal data from the patient;
step (d) further includes calculating a third indicator based on the ECG signal data, the third indicator being indicative of the heart rate of the patient; and
step (e) includes producing the composite indication from the first, second, and third indicators.

4. A method according to claim 1, wherein
step (b) further includes obtaining EMG signal data from the patient;
step (d) further includes calculating a fourth indicator based on the EMG signal data, the fourth indicator being indicative of electromyographic activity in the patient; and
step (e) includes producing the composite indication from the first, second, and fourth indicators.

5. A method according to claim 3, wherein
step (b) further includes obtaining EMG signal data from the patient;
step (d) further includes calculating a fourth indicator based on the EMG signal data, the fourth indicator being indicative of electromyographic activity in the patient; and
step (e) includes producing the composite indication from the first, second, third, and fourth indicators.

6. A method according to claim 1, wherein step (d) includes obtaining a measure of the rate at which changes occur in the bioimpedance signal data as the second indicator.

7. A method according to claim 6, wherein step (d) includes the steps of:
differentiating the bioimpedance signal data to obtain derivation signal data representing changes in the bioimpedance signal data;
defining a threshold for the derivation signal data; and
determining the rate at which the derivation signal data exceeds the threshold.

8. A method according to claim 7, further comprising a step of suppressing the range of the derivation signal data to obtain suppressed derivation signal data, wherein the threshold is defined for the suppressed derivation signal data.

9. A method according to claim 7, further comprising a step of adapting the derivation signal data between a minimum and a maximum value to obtain adapted derivation signal data, wherein the threshold is defined for the adapted derivation signal data.

10. A method according to claim 7, further comprising the steps of
suppressing the range of the derivation signal data to obtain suppressed derivation signal data; and
adapting the suppressed derivation signal data between a minimum and a maximum value to obtain suppressed and adapted derivation signal data,
wherein the threshold is defined for the suppressed and adapted derivation signal data.

11. A method according to claim 1, wherein step (c) includes obtaining a measure of the entropy of the EEG biopotential signal data as the first indicator.

12. A method according to claim 4, wherein step (d) includes obtaining a measure of the power spectrum of the EMG signal data as the fourth indicator.

13. A method according to claim 1, wherein the EEG biopotential signal data and the bioimpedance signal data are obtained through at least one sensor attached to the patient, the at least one sensor including at least one electrode used for obtaining both the EEG biopotential signal data and the bioimpedance signal data.

14. A method according to claim 13, wherein steps (a) and (b) are performed simultaneously.

15. A method according to claim 14, wherein step (a) includes obtaining a biopotential signal from the patient, step (b) includes supplying electric current at a first frequency to the patient to obtain the bioimpedance signal data, and step (a) further includes removing electrical phenomena of the first frequency from the biopotential signal.

16. A method according to claim 13, wherein steps (a) and (b) are performed on a time division basis.

17. A method according to claim 1, wherein the first indicator and the set of indicators are supplied as input data to a device for administering drugs.

18. An apparatus for monitoring a state of anesthesia or sedation resulting from the administration of one or more drugs to a patient, the drug or drugs inducing the state of anesthesia or sedation by altering the state or functioning of one or both of the cortex of the brain or the sub-cortical components of the nervous system, the apparatus comprising:
means for obtaining cortex-related EEG biopotential signal data from the patient;
means for obtaining subcortex-related biosignal data from the patient, the subcortex-related biosignal data including at least bioimpedance signal data;
means for analyzing the cortex-related EEG biopotential signal data to obtain a first indicator comprising a measure of the complexity of the EEG biopotential signal data;
means for analyzing the subcortex-related biosignal data to obtain a set of indicators indicative of subcortex-related activity in the patient, the set of indicators including at least a second indicator calculated based on the bioimpedance signal data; and
means for producing a composite indication based on the first indicator and the set of indicators.

19. An apparatus according to claim 18, wherein the means for obtaining the subcortex-related biosignal data comprises means for obtaining only a bioimpedance signal from the patient, the bioimpedance signal including the bioimpedance signal data.

20. An apparatus according to claim 18, wherein the means for obtaining the subcortex-related biosignal data includes first measurement means for obtaining at least one bioimpedance signal and at least one biopotential signal from the patient, the at least one bioimpedance signal including the bioimpedance signal data, and the at least one biopotential signal including at least one type of signal data from a group including ECG signal data and EMG signal data.

21. An apparatus according to claim 18, wherein the apparatus comprises a plurality of measurement electrodes of which at least one is common to the means for obtaining the cortex-related EEG biopotential signal data and to the means for obtaining the subcortex-related biosignal data.

22. An apparatus according to claim 21, wherein the means for obtaining the cortex-related EEG biopotential signal data and the means for obtaining the subcortex-related biosignal data from the patient comprise, in total four patient electrodes.

23. An apparatus according to claim 18, wherein the means for analyzing the cortex-related EEG biopotential signal data and the means for analyzing the subcortex-related biosignal data are operably connected to a device configured to administer drugs to the patient.

24. A method according to claim 1 wherein:
step (b) is further defined as obtaining subcortex-related biosignal data comprising skin conductivity signal data and
step (d) is further defined as calculating a second indicator based on the skin conductivity signal data.

25. A method according to claim 24 wherein
step (b) further includes obtaining ECG signal data from the patient;
step (d) further includes calculating a third indicator based on the ECG signal data, the third indicator being indicative of the heart rate of the patient; and
step (e) includes producing the composite indication from the first, second, and third indicators.

26. A method according to claim 24, wherein
step (b) further includes obtaining EMG signal data from the patient;
step (d) further includes calculating a fourth indicator based on the EMG signal data, the fourth indicator being indicative of electromyographic activity in the patient; and
step (e) includes producing the composite indication from the first, second, and fourth indicators.

27. A method according to claim 25, wherein
step (b) further includes obtaining EMG signal data from the patient;
step (d) further includes calculating a fourth indicator based on the EMG signal data, the fourth indicator being indicative of electromyographic activity in the patient; and
step (e) includes producing the composite indication from the first, second, third, and fourth indicators.

28. An apparatus according to claim 18 wherein the means for obtaining the subcortex-related biosignal data comprises means for obtaining skin conductivity bioimpedance signal data.

29. An apparatus according to claim 28, wherein the means for obtaining the subcortex-related biosignal data includes first measurement means for obtaining at least one bioimpedance signal and at least one biopotential signal from the patient, the at least one bioimpedance signal including the skin conductivity bioimpedance signal data, and the at least one biopotential signal including at least one type of signal data from a group including ECG signal data and EMG signal data.

* * * * *